United States Patent [19]

Verdini et al.

[11] Patent Number: 4,816,560
[45] Date of Patent: Mar. 28, 1989

[54] PARTIALLY RETRO-INVERTED TUFTSIN ANALOGUES, METHOD FOR THE PREPARATION THEREOF AND PHARMACEUTICAL COMPOSITIONS CONTAINING THEM

[75] Inventors: Antonio S. Verdini, Monterotondo; Fabio Bonelli; Antonello Pessi, both of Rome; Franco Cardinali, Ostia Lido; Diana Boraschi, Berardenga; Stefano Censini, Serre di Rapolano; Romano Di Trapani, Monterotondo, all of Italy

[73] Assignees: Eniricerche S.p.A., Milan; Sclavo S.p.A., Siena, both of Italy

[21] Appl. No.: 74,054

[22] Filed: Jul. 16, 1987

[30] Foreign Application Priority Data

Jul. 16, 1986 [IT] Italy .................... 21145 A/86
Jul. 16, 1986 [IT] Italy .................... 21143 A/86

[51] Int. Cl.$^4$ ................................. C07K 5/02
[52] U.S. Cl. ........................... 530/323; 530/331; 530/332
[58] Field of Search .................. 530/323, 331, 332

[56] References Cited

U.S. PATENT DOCUMENTS

| | | | |
|---|---|---|---|
| 4,439,360 | 3/1984 | Verdini et al. | 530/329 |
| 4,560,505 | 12/1985 | Pinori et al. | 530/328 |
| 4,585,586 | 4/1986 | Di Trapani et al. | 530/323 |
| 4,638,046 | 1/1987 | Verdini et al. | 530/332 |
| 4,716,149 | 12/1987 | Bonelli et al. | 514/13 |
| 4,728,725 | 3/1988 | Sisto et al. | 530/314 |

*Primary Examiner*—Delbert R. Phillips
*Attorney, Agent, or Firm*—Birch, Stewart, Kolasch & Birch

[57] ABSTRACT

New partially retro-inverted tuftsin analogues of general formula I

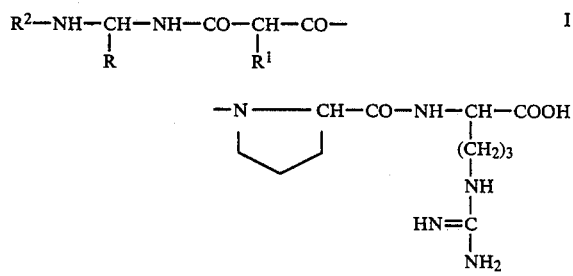

wherein
R represents the side-chain of the amino acids threonine, methionine or leucine
$R^1$ represents the side-chain of the amino acids lysine or arginine
$R^2$ is hydrogen or a metabolically labile acyl group,
all the asymmetric carbon atoms are either of the S- or R-configuration, or, alternatively, the first, third, and fourth asymmetric carbons, starting from the N-terminal residue, are of the S-configuration while the second one is of the R- or (R,S)-configuration, and the corresponding pharmacologically acceptable salts, esters and amides. The new compounds which share the same pharmacological properties of tuftsin, are much more stable toward the enzymatic degradation than the parent molecule.

8 Claims, No Drawings

PARTIALLY RETRO-INVERTED TUFTSIN ANALOGUES, METHOD FOR THE PREPARATION THEREOF AND PHARMACEUTICAL COMPOSITIONS CONTAINING THEM

The present invention refers to new partially retroinverted inverted tuftsin analogues of general formula I

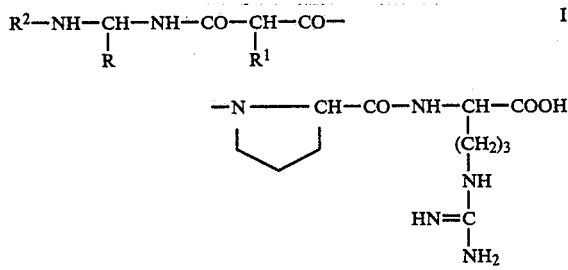

wherein

R represents the side-chain of the amino acids threonine (R=—CH(OH)CH$_3$), methionine (R=—CH$_2$—CH$_2$—S—CH$_3$) or leucine (R=—CH$_2$—CH(CH$_3$)$_2$), R$^1$ represents the side-chain of the amino acids lysine (R$^1$=—(CH$_2$)$_4$—NH$_2$) or arginine (R$^1$=—(CH$_2$)$_3$—NH—C(=NH)NH$_2$)

R$^2$ is hydrogen or a metabolically labile acyl radical, and all the asymmetric carbon atoms are of the same S— or R— configuration, or the first, third, and fourth asymmetric carbons starting from the N-terminal residue are of the S— configuration while the second is of the R— or (R,S)-configuration, and the corresponding pharmacologically acceptable salts, esters and amides.

The present invention is also directed to a method of preparation of the new compounds and to the pharmaceutical compositions containing them.

For the purposes of the present invention, the term "metabolically labile acyl radical", as used above, designates any acyl radical which is rapidly cleaved off in the first steps of the metabolic pathway and which is relatively non-toxic and innocuous to mammals at dosages consistent with good biological activity.

A preferred group of compounds of the present invention comprises those compounds of formula I wherein R and R$^1$ are as defined above and R$^2$ is a hydrogen atom, and the corresponding pharmacologically acceptable salts, esters and amides.

A particularly preferred group of compounds of the invention comprises those compounds of formula I wherein R is as defined above, R$^1$ represents the side-chain of the amino acid lysine and R$^2$ is hydrogen, and the corresponding pharmacologically acceptable salts, esters, and amides.

A most preferred group of compounds of the invention comprises those compounds of formula I wherein R represents the side-chain of the amino acid threonine, R$^1$ represents the side-chain of the amino acid lysine, and R$^2$ is hydrogen, and the corresponding pharmacologically acceptable salts, esters and amides. Tuftsin is a natural tetrapeptide, characterized by the sequence Thr-Lys-Pro-Arg, which has been isolated in 1970 by Najjar and coworkers (see Najjar V.A. and Nishioka K., Nature, Vol.228, p.672 (1970)).

It is freed from a particular immunoglobulin, leukokinin, by the action of two enzymes, tuftsin-endocarboxypeptidase, a spleen enzyme which acts upon circulating leukokinin and cleaves the Arg-Glu bond at the carboxyterminal of tuftsin, and leukokininase, a membrane enzyme of neutrophils, monocytes and macrophages which cleaves the Lys-Thr bond thus setting free the aminoterminus of tuftsin. Its principal biological effect is to activate phagocytic cells, principally the macrophages, but it is fully active only when it is set free from the carrier leukokinin molecule (Najjar V. A. - Advances in Enzymology - 41 p.129-78 (1974); Najjar V. A. - J. Pediatr. - 87 p.1121-24 (1975)). Tuftsin binds to specific receptors on the outer membrane of phagocytic cells, after which it is internalized and becomes susceptible to the action of cytoplasmic enzymes. The most active enzyme is an aminopeptidase that cleaves off the threonine residue to yield the tripeptide Lys-Pro-Arg, which is an inhibitor of tuftsin activity (Spirer Z. et al. J.Clin.Invest., 55, p.198-200 (1975) and Fridkin M. et al. - Biochim.Biophys.Acta, 496, p.203-11 (1977)). Since 1970, and particularly in the last ten years, tuftsin has been thoroughly investigated. In particular, the biological effects of tuftsin have been better elucidated, and a more detailed pharmacological profile of this compound has been drawn up. Furthermore several tuftsin analogues have been synthesized and structure-activity and structure-stability relationships have been shown. As far as the former aspect is concerned, it has been recognized that tuftsin stimulates not only phagocytosis but also the antibacterial activity (Martinez J. et al. - Eur.J.Med. Chem.- Chim.Ther., 12, p.511-6 (1977)) and the tumoricidal activity of the macrophages (Nishioka K. Br.J.Cancer, 39(3), p.342-45, (1979); Najjar V. A. & Linehan L. - Tumoricidal Activity of Tuftsin - Proc. XIII Int.Cancer Congr. p.314 (1982)), thus showing a very promising clinical potential as an immunostimulating, antibacterial and antitumor drug. As far as the latter aspect is concerned, structure-activity correlation studies showed that it is possible to replace threonine at position 1 of the tuftsin sequence with methionine or leucine while retaining stimulation of phagocytosis (Matsuura S. et al. - Chem.Abst. 83 114937 e). These compounds however have the same stability problems as tuftsin. It has been demonstrated in fact that stimulation of bactericidal activity of macrophages by tuftsin is greatly accelerated during the initial phase (15 minutes) of infection and that this stimulatory effect does not last longer because tuftsin is rapidly destroyed by cell enzymes. It has been observed, furthermore, that high doses of tuftsin inhibit its activity by decreasing macrophage immune function in vitro and depressing the antibody responses in mice. This can be explained by the fact that the rapid metabolic degradation of tuftsin results in the liberation of the more stable tripeptide Lys-Pro-Arg which was shown to be an inhibitor of tuftsin activity and to compete with the tetrapeptide for cellular receptors (Florentin I. et al. - Properties of Tuftsin - Antineoplastic, immunogenic and other effects of the tetrapeptide tuftsin: a natural macrophage activator-Annals of the New York Academy of Sciences - Volume 419 - Ed. V. A. Najjar and M. Fridkin - 1983).

An attempt to overcome said problems and increase the enzymatic stability of the tuftsin analogue has been made by synthesizing the wholly retro-inverted tuftsin derivative, which however proved to be inactive (Hisatsune K. at al. - Chem. Pharm. Bull., 26, p.1006-7 (1978)).

It has now been found that the compounds of formula I of the present invention, obtained by reverting only the peptide bond linking the amino acid residue at position 1 to that at position 2, maintain the same pharmacological profile as the corresponding compounds wherein said bond has not been reverted while showing to be more stable to enzymatic degradation. The new compounds of the present invention are prepared by condensing a malonic acid derivative of formula II

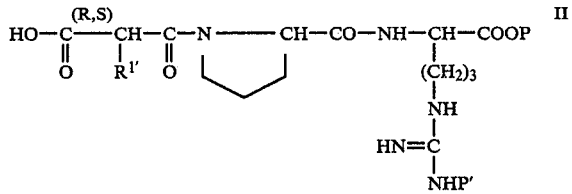

wherein
R$^{1'}$ represents the side-chain of the amino acids lysine or arginine wherein the amino or guanidino group, respectively, is suitably protected
P is an easily removable carboxyl protecting group
P' is an easily removable guanidino protecting group, and the configuration of the asymmetric carbons is as indicated above,
with an amide of formula III

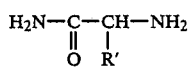

wherein
R' represents the side-chain of the amino acids threonine, methionine, or leucine wherein the functional groups, if any, are suitably protected and the asymmetric carbon is of the R- or S-configuration, in the presence of a suitably selected coupling agent, followed by reaction of the thus obtained compound of formula IV

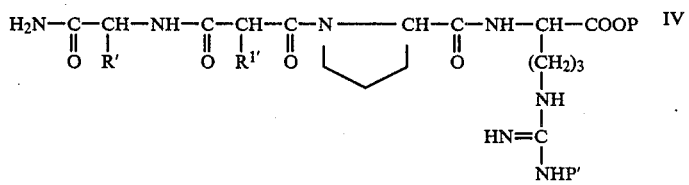

wherein
R', R$^{1'}$, P, and P' as well as the configuration of the asymmetrical carbon atoms are as defined above, with (1,1-bis-trifluoroacetoxy)iodobenzene (TIB) to selectively convert the terminal carbamyl group to a primary amino group, followed by optional acylation of the terminal amino function with a metabolically labile acyl group, and removal of the protecting groups. If a compound of formula I wherein R$^2$ is hydrogen is desired and the acylation step is therefore no longer needed, the sequential arrangement of the amide/amine conversion and deprotection steps may suitably be reverted. According to a preferred embodiment of the invention, in fact, when a compound of formula I is desired wherein R$^2$ is a hydrogen atom, the compound of formula IV, obtained by condensing fragments II and III, is deprotected first and then reacted with TIB to give the desired retro-inverso peptide of formula I. The new intermediates of formula IV, wherein R', R$^{1'}$, P, and P' are as defined above, as well as the corresponding derivatives wherein the protecting groups have been suitably removed, represent a further object of the present invention. In particular, said products, besides being useful as intermediates, proved to have an immunostimulating activity comparable to that of tuftsin itself.

As for a detailed description of the above sketched process, the first step may conveniently be carried out according to any of the peptide synthesis methods known in literature. Optimum results, in terms of yields and purity of the products, have been obtained by preparing first an activated ester of the carboxylic acid II, e.g. by the addition of a slight excess of N-hydroxy-benzotriazole (HOBT) to a solution of the acid of formula II, contacting then the activated ester with the coupling agent, typically dicyclohexylcarbodiimide (DCCI), and finally with the reaction partner of formula III. Conventional polar aprotic organic solvents capable of dissolving the reactants and which do not interfere with the reaction course, are suitably employed in this condensation reaction, which can be carried out conveniently at room temperature. Solvents of choice are the halogenated hydrocarbons, e.g. methylene chloride, chloroform, dichloroethane, etc., optionally mixed with more polar organic solvents such as dimethylformamide, dimethylsulfoxide, acetonitrile, and the like. When the condensation reaction, whose course can be easily monitored by tlc, is complete, the intermediate product of formula IV can be recovered according to conventional recovery techniques. In particular, when DCCI is used as the coupling agent, these involve evaporating off the solvent, dissolving the residue in tetrahydrofuran, cooling the reaction mixture, removing the cyclohexylurea precipitate by filtration, carefully washing the filtrate with slightly basic and slightly acidic aqueous solutions and evaporating off the organic solvent.

The reaction of the thus obtained product with TIB is then carried out according to the method described in Italian patent application No. 25755 A/81, which involves reaction of the amide substrate with a slight excess of TIB in water/inert organic solvent mixtures such as for instance water/dimethylformamide, water/acetonitrile, and the like. The reaction is carried out while bubbling an inert gas through the reaction mixture and monitoring the reaction course by tlc.

At the end of the reaction, the organic solvent is removed and the product is easily recovered by freeze-drying. Acylation of this product can then be carried out, using the active esters of the acid R$^2$COOH such as for instance the p-nitrophenyl or 2,4,5-trichlorophenyl esters. Deprotection is then carried out according to known methods. In general, when conventional protecting groups are employed, such as t-butyl or t-amyl groups for carboxyl protection and optionally for threonine hydroxyl protection, and tert-butoxycarbonyl, benzyloxycarbonyl and the like groups are employed for amino protection, these groups are conveniently removed by acidolysis in mildly acidic conditions such as for instance with diluted hydrochloric acid in acetic acid, with trifluoroacetic acid or with trifluoroacetic acid/methylene chloride mixtures in the presence of varying percentages of anisole, thioanisole, or resorcinol used as scavengers to entrap the t-butyl, t-amyl or benzyl carbocations which form.

Once deprotection is over, the desired product of formula I is recovered and purified according to conventional chromatographic methods and techniques. Particularly suitable to this purpose is reversed-phase chromatography. Homogeneity of the thus obtained products is checked by tlc and HPLC, while their purity is further tested by amino acid analysis and NMR spectroscopy.

As anticipated above, when a compound of formula I is desired wherein $R^2$ is hydrogen, the sequential arrangement of the amide/amine conversion and deprotection steps is preferably reverted. The general methods for carrying out each step are however the same.

The starting compounds of formulas II and III may be easily prepared either starting from commercially available compounds or from compounds prepared on purpose by methods known or analogous to methods known in peptide and organic synthesis chemistry. More particularly, the malonyl derivative of formula II is prepared by a series of condensation/deprotection steps carried out according to methods and techniques known in the literature and widely employed in the synthesis of partially retro-inverted peptides, starting from the malonyl derivative V:

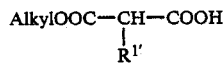

V wherein $R^{1'}$ is as defined above.

In its turn the malonyl derivative V is easily prepared from the corresponding di-ester by partial hydrolysis under controlled alkaline conditions. The diester is obtained through reaction of the alkaline salt of a malonic acid di-lower alkyl ester with a suitably selected halide of formula $R^{1'}$-X wherein $R^{1'}$ is as defined above and X is preferably chloro. More particularly, the malonic acid di-lower alkyl ester is added to an alkanol solution of the alkali metal, and the reaction partner $R^{1'}$-X is then added thereto. When the reaction is complete, the desired product is recovered by washing with water and evaporating off the organic solvent.

Partial hydrolysis of the thus obtained intermediate, typically in ethanol/KOH, affords the mono-ester of formula V.

As the compounds of the present invention have at least 4 asymmetric carbon atoms in their molecule (those marked by an asterisk in the formula below), plural isomeric forms may exist According to a preferred embodiment of the present invention the absolute configuration of the terminal amino acids Pro-Arg is the L-configuration and the compounds of formula I wherein the last two asymmetric carbon atoms are of the L-configuration can be easily obtained using the suitable L-proline and L-arginine derivatives in the preparation of the starting compound of formula II. As the use of the 2-substituted malonyl residue in the above defined process yields a mixture of isomers of formula I, this can be resolved, if desired, into the single isomers, generally by reversed-phase HPLC.

The compounds of the present invention of formula I may form basic and acid salts with a number of inorganic and organic bases and acids. Said basic salts include for instance the alkali metal salts, such as sodium or potassium, or earth-alkaline salts such as calcium or magnesium, while the acid salts include the acid addition salts with inorganic acids such as HCl, HBr, $H_2SO_4$, $H_3PO_4$, sulphonic organic acids and carboxylic organic acids such as acetic acid, oxalic acid, pivalic acid and the like acids. The physiologically acceptable salts are obviously preferred as they can be employed in therapy as described later on. These and other salts, which are not necessarily physiologically acceptable, may however be employed for isolating or purifying the compounds of formula I. Said salts are easily prepared by reacting the compound of formula I as the free acid or base with one or more equivalents of the suitably selected base or acid in a solvent or reaction medium in which the salt is insoluble or in a solvent which can be easily removed. Following a particularly advantageous technique, said salt formation is carried out in water and the thus obtained salt is recovered by freeze-drying.

The corresponding esters and amides of the compounds of formula I are also enclosed within the scope of the present invention. Said derivatives include the alkyl, di-(alkyl)aminoalkyl, acylaminoalkyl, acyloxyalkyl, benzyl and substituted benzyl esters and the benzyl, phenethyl, and mono- and di-N-alkyl amides. A preferred group of said derivatives includes the esters of the compounds of formula I wherein the ester group is easily hydrolysed in acidic conditions, such as for instance the t-butyl or t-amyl ester, because these compounds can be used as intermediates.

The compounds of formula I, including the pharmaceutically acceptable esters, amides and salts, are active as immunostimulating agents. This activity has been demonstrated in vitro by means of the macrophage ($M\phi$) phagocytic stimulation assay. This assay, carried out in comparison with tuftsin, has been performed according to a modification of the method described by Bar-Shavit et al. in J.Cell.Physiol., 100, p.55 (1979). More particularly, peritoneal $M\phi$ from normal

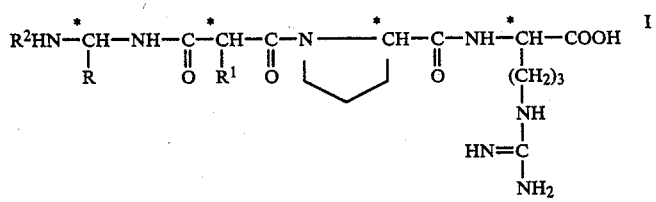

I

The above summarized process, however, is a stereoselective process i.e. the configuration of each starting fragment, excluding the 2-substituted malonyl residue which is employed as a racemate, is retained in each step.

C3H/HeN mice are harvested by washing of the peritoneal cavity and purified by adherence as described in J.Immunol., 132, p.1987 (1984). Monolayers of $1 \times 10^6$ adherent peritoneal cells (95–98% of the monocyte-$M\phi$ series as judged by morphology and latex phagocytosis)

are cultured for 20 h at 37° C. in RPMI-1640 medium supplemented with 50 μg/ml gentamycin, 25 mM HEPES buffer, 2 mM L-glutamine and 10% heat-inactivated fetal bovine serum (FBS). At the end of the incubation, Mφ are washed and then exposed for 15 minutes at 37° C. to 1.3 ml/plate of culture medium either alone (blank) or containing tuftsin or a compound of the invention at different concentrations. A $1.5 \times 10^8$ cells/ml suspension of killed yeast cells (Zymosan)(0.2 ml) is then added to the plates. Mφ are incubated for 60 minutes at 37° C., then washed, fixed (2% glutaraldehyde in PBS, 30 minutes, 4° C.) and stained. The percentage of phagocyting Mφ and the number of ingested Zymosan cells is measured with an optical microscope equipped with a 100x immersion objective. In a representative experiment aimed at comparing the activity of tuftsin with that of the corresponding retro-inverso analogue of example 1, it has been observed that all Mφ were capable of phagocyting zymosan in the above described conditions. However, in the presence of tuftsin or of the compound of example 1, the number of ingested yeast cells significantly increased and was linearly dependent on peptide concentration. In particular it has been observed that the compound of Example 1 at a concentration of $3 \times 10^{-7}M$ resulted in $2.2 \times 10^3$ ingested zymosan cells per 100 macrophages (170% of the control), while at the concentration of $10^{-6}M$ gave $2.44 \times 10^3$ ingested zymosan cells per 100 phagocyting macrophages (188% of the control).

As the poor therapeutical applicability of tuftsin is mainly due to its low stability and to the consequent rapid loss of biological activity, the phagocytosis assay has been repeated comparing the activity of tuftsin and its retro-inverso analogue of Example 1, stored for 14 days in solution at 4° C. In these conditions tuftsin, as expected, was devoid of activity, while, on the contrary, the phagocytosis stimulation induced by the compound of example 1, was still significant even if less than above. At the concentration of $10^{-6}M$ in fact the compound of Example 1 gave a number of ingested zymosan cells per 100 phagocyting macrophages of $1.8 \times 10^3$ (with an immunopotentiating effect corresponding therefore to 136% of the control).

The compounds of the present invention are therefore useful in all those cases where it is necessary or advisable to stimulate the defense mechanisms against infectious agents or tumor cells. For said pathological conditions, a treatment schedule providing for a single dose, repeated every 4-8 days, can conveniently be employed where the dosage, which obviously depends on the pathological condition and its severeness, the administration route, the particular compound of formula I administered and any concomitant therapeutical treatment, will be generally comprised between 0.001 and 5 mg of active principle per Kg of body weight and preferably between 0.01 and 2 mg/Kg.

The compounds of formula I can be administered parenterally, and in particular intravenously and intraperitoneally, or orally. They can therefore be formulated in suitable solid or liquid dosage forms, such as for instance tablets, capsules or elixirs for the oral administration and sterile solutions or suspensions for parenteral administration.

Said dosage forms, which will preferably contain from 0.01 to 300 mg of a compound of formula I as the active ingredient per unit dosage form, together with the conventional vehicles, excipients, preservatives, and the like agents, are prepared according to methods well known to the industrial pharmacy expert.

The compounds of the present invention may also be formulated in admixture with other therapeutically effective compounds. For instance, in the treatment of bacterial infections in patients with impaired immune functions, it may be advisable to use a formulation containing, besides the antibiotic agent effective against the microorganism causing the infection, a suitable dose of an immunostimulating compound of formula I.

The following example which is only aimed at better describing the preparation of a representative compound of the invention, should in no way be considered as a limitation to the scopes thereof.

For the sake of clarity, the following abbreviations have been used throughout the text. Z=benzyloxycarbonyl; $Bu^t$=tert-butyl; Boc=tert-butoxycarbonyl; AcOEt=ethyl acetate; Mtr=(2,3,6-trimethyl-4-methoxyphenyl)sulphonyl; EtO=ethoxy; Bz=benzyl; NMM=N-methylmorpholine; HOBT=N-hydroxybenzotriazole; DMF=dimethylformamide; DCCI=-dicyclohexylcarbodiimide; EtOH=ethyl alcohol; THF=tetrahydrofuran; DCU=dicyclohexylurea; TFA=trifluoro-acetic acid; $Et_2O$=ethyl ether; TIB=(1,1-bis-trifluoroacetoxy)iodobenzene;

EXAMPLE 1

{(2RS)-2-[N-(1-amino-2-hydroxy-propyl)carbamyl]-6-amino}-hexanoyl-L-prolyl-L-arginine
gThr-(R,S)mLys-L-Pro-L-Arg-OH (a) N-benzyloxycarbonyl-O-tert-butyl-D-threonineamide (Z-D-Thr($Bu^t$)-$NH_2$)

Concentrated $H_2SO_4$ (0.1 ml) and isobutylene (35 ml, 390 mmol) are added to a suspension of N-benzyloxycarbonyl-D-threonineamide (4.2 g, 16.6 mmol) in methylene chloride (35 ml) kept in a pressure resistant vessel cooled with dry ice/acetone. The reaction vessel is sealed and the temperature is allowed to raise up to the room value. After 4 days, excess isobutylene is evaporated off and the organic solution is washed with aqueous 5% $Na_2CO_3$ ($3 \times 30$ ml), 5% citric acid (20 ml) and then with water up to pH 6. The organic phase is dried over $MgSO_4$ and concentrated to dryness yielding the compound of the title as a clear oil (4.62 g, 90%).

NMR and mass spectroscopy confirm the assigned structure. HPLC and tlc confirm that the product is unitary.

(b) O-tert-butyl-D-threonineamide (H-D-Thr($Bu^t$)-$NH_2$)

10% Pd/C (1.5 g) is added to a solution of the compound obtained in step (a) in MeOH (200 ml), and hydrogen is bubbled through the reaction mixture for 1.5 h, checking the disappearance of the starting compound by tlc. When the reaction is over, excess hydrogen is removed by passing a nitrogen stream through the mixture, the reaction mixture is filtered over celite and the filtrate is concentrated to dryness thus yielding O-tert-butyl-D-threonineamide (2.55 g, 99%). Both mass and NMR spectra confirm the assigned structure.

(c) mono-ethyl ester of (2RS)-2-[(4-t-butoxy-carbonyl-amino)butyl]malonic acid OEt-(R,S)mLys(Boc)-OH A solution of 4-chloro-butylamine hydrochloride (14.38 g, 0.1 mol) in dioxane/water (100 ml, 2/1, v/v) is slowly added to a vigorously stirred mixture of di-(tert-butyl)carbonate (24 g, 0.11 mol), 1N $Na_2CO_3$ (100 ml) and dioxane/water (200 ml, 2/1, v/v) cooled to 0° C. When the addition is over, the raction mixture is stirred at room temperature for an additional hour, dioxane is removed under vacuum and the aqueous phase is extracted a few times with ethyl acetate. From the organic solution N-[(tert-butoxy)carbonyl]-4-chloro-butylamine, as an oily product (21 g), is recovered. Sodium metal (0.28 g, 0.012 mol) is dissolved in absolute ethyl alcohol (9 ml) under nitrogen atmosphere. The mixture is heated to 60° C. and malonic acid di-ethyl ester (3.8 g, 0.024 mol) is slowly dripped in. N-[tert-butoxy)carbony]-4-chloro-butyl-amine (2.5 g, 0.012 mol) is then gradually added to the resulting mixture at room temperature. The reaction mixture is stirred at room temperature for 2 hours and at the reflux temperature for 6 hours, then it is poured into ethyl acetate/water (100 ml, 1/1, v/v). The organic phase is recovered, washed several times with water and dried over MgSO$_4$. The organic solvent is removed under vacuum (0.5 mBar) at 100° C., yielding a raw oily product which is purified by reversed-phase HPLC using an RP-18 resin and eluting with an aqueous phase modified with CH$_3$CN (45% by volume).

(2 R,S)-2-[(4-tert-butoxy-carbonyl-amino)butyl]-malonic acid diethyl ester (1.31 g) is thus obtained as a pure product.

An ethanol solution of KOH (4.31 ml, 0.417M) is very slowly added to a solution of (2R,S)-2-[(4-tert-butoxycarbonylamino)butyl]malonic acid diethyl ester (1.2 g, 3.6 mmol) in absolute ethyl alcohol (7 ml). The reaction mixture is allowed to stand overnight, then is diluted with water and ethanol is evaporated off. The pH is brought to 8 by the addition of a 5% NaHCO$_3$ solution and the reaction mixture is extracted with AcOEt (4×50 ml) in order to recover the unreacted starting compound. The aqueous solution is brought to pH 3 by the addition of citric acid and is extracted with AcOEt (6×50 ml). The organic extracts are combined, washed with water up to pH 6 and concentrated to dryness yielding the compound of the title as a colorless oil (1.6 g, 88%). The mass and NMR spectra are in agreement with the assigned structure.

(d) N$^\alpha$-benzyloxycarbonyl-N$^G$-(2,3,6-trimethyl-4-methoxy-phenyl)sulphonyl-L-arginine tert-butyl ester (Z-Arg(N$^G$-Mtr)-OBu$^t$)

POCl$_3$ (7.06 ml, 77 mmol) is dripped into a solution of N$^\alpha$-benzyloxycarbonyl-N$^G$-(2,3,6-tri-methyl-4-methoxyphenyl)sulphonyl-L-arginine (3.6 g, 7 mmol) and pyridine (6.94 ml, 86 mmol) in tert-butyl alcohol (100 ml) kept under nitrogen atmosphere and cooled to −5° C. The reaction mixture is allowed to stand at room temperature overnight and then it is diluted with a mixture of ethyl acetate and water 1/1. The organic phase is separated and washed first with a 5% NaHCO$_3$ aqueous solution (16×100 ml) and then with water up to neutral pH. The organic phase is dried over MgSO$_4$ and the solvent is evaporated off giving the compound N$^\alpha$-benzyloxycarbonyl-N$^G$-(2,3,6-trimethyl-4-methoxy-phenyl)sulphonyl-L-arginine tert-butyl ester (1 g, 25%).

(e) N$^G$-(2,3,6-trimethyl-4-methoxy-phenyl)sulphonyl-L-arginine tert-butyl ester (H-Arg(N$^G$-Mtr)-OBu$^t$)

By following substantially the same procedure as in step (b) but starting from the compound obtained in step (d), N$^G$-(2,3,6-tri-methyl-4-methoxyphenyl)-sulphonyl-L-arginine tert-butyl ester (612 mg, 81%) is obtained as a white foam.

$[\alpha]_D^{20}$ −0.84° (c=1.18% CH$_2$Cl$_2$)

The NMR spectrum confirms the assigned structure.

(f) [(2RS)-2-ethoxy-carbonyl-6-tert-butoxy-carbonyl-amino]hexanoyl-L-proline benzyl ester (EtO-(R,S)mLys(N$^\epsilon$-Boc)-L-Pro-OBz)

The compound obtained in step (c) (0.6 g, 1.98 mmol) is dissolved in CH$_2$Cl$_2$ (40 ml) and a solution of HOBT (0.325 g, 2.4 mmol) in DMF (2 ml) and CH$_2$Cl$_2$ (3 ml) is added thereto. The reaction mixture is cooled to 0° C. and a solution of DCCI (0.495 g, 2.4 mmol) in CH$_2$Cl$_2$ (5 ml) is added thereto at this temperature. The reaction mixture is stirred at 0° C. for 30 minutes and then at room temperature for additional 20 minutes. The activated ester thus prepared is filtered into a reaction flask containing a solution of proline benzyl ester hydrochloride (0.532 g, 2.2 mmol) in CH$_2$Cl$_2$ (60 ml), to which NMM (0.242 ml, 2.2 mmol) necessary to remove the hydrochloride has just been added. The mixture is stirred at room temperature overnight, the solvent is then evaporated off and the oily residue is taken up in a small amount of AcOEt and kept at −25° C. for one hour. The precipitate is removed by filtration and the filtrate is diluted with an additional amount of AcOEt, washed with 5% aqueous NaHCO$_3$ (5×100 ml), with 5% aqueous citric acid (3×50 ml) and finally with water up to pH 6–6.5. The organic phase is dried over MgSO$_4$ and then concentrated to dryness under vacuum yielding [(2 RS)-2-ethoxy-carbonyl-6-tert-butoxycarbonyl-amino]hexanoyl-L-proline benzyl ester as a yellow oil (0.88 g, 90%). Mass and NMR spectra confirm the proposed structure.

(g) [(2 R,S)-2-ethoxycarbonyl-6-(tert-butoxycarbonyl-amino)]-hexanoyl-L-proline (OEt-(R,S)mLys(N$^\epsilon$-Boc)-L-Pro-OH)

This compound is prepared through hydrogenolysis of the compound obtained in the foregoing step, following substantially the same procedure as in step (b).

The thus obtained product (91%) has $[\alpha]_D^{20}$ = −38.18° (c=1.32 % in CH$_2$Cl$_2$).

(h) [(2R,S)-2-ethoxycarbonyl-6-(tert-butoxycarbonyl-amino)]hexanoyl-L-prolyl-(N$^G$-(2,3,6-trimethyl-4-methoxyphenyl)sulphonyl)-L-arginine tert-butyl ester (OEt-(R,S)mLys(N$^\epsilon$-Boc)-L-Pro-L-Arg(N$^G$-Mtr)-OBu$^t$)

A solution of HOBT (0.261 g, 1.93 mmol) in CH$_2$Cl$_2$ (3 ml) and DMF (0.5 ml) is added to a solution of the compound prepared in step (g) (0.66 g, 1.64 mmol) in CH$_2$Cl$_2$ (50 ml), the obtained mixture is cooled to 0° C. and DCCI (0.398 g, 1.93 mmol) is added thereto. The reaction mixture is then stirred at 0° C. for 30 minutes and at room temperature for further 20 minutes. The thus obtained activated ester is filtered into a reaction flask containing a solution of the compound of step (e) (0.590 g, 1.3 mmol) in CH$_2$Cl$_2$ (60 ml). When the reaction, whose course can be easily monitored by tlc, is over, the solvent is evaporated off, the residue is taken up in a small amount of AcOEt and cooled to −25° C. for one hour. The precipitate is removed by filtration, the filtrate is diluted with additional AcOEt (100 ml) and washed with a 5% NaHCO$_3$ aqueous solution (4×100 ml), with a saturated NaCl solution and finally with water up to neutral pH. The organic solution is dried over MgSO$_4$ and the solvent is evaporated under vacuum yielding the desired compound (0.857 g, 80%) as a yellow oil.

(i) [(2R,S)-2-carboxy-6-(tert-butoxycarbonylamino)]-hexanoyl-L-prolyl-[N$^G$-(2,3,6-trimethyl-4-methoxyphenyl)sulphonyl]-L-arginine tert-butyl ester (HO-(R,S)mLys(N$^\epsilon$-Boc)-L-Pro-L-Arg(N$^G$-Mtr)-OBu$^t$)

1M KOH in absolute ethanol (2 ml, 2 mmol) is added to a stirred solution of the compound obtained in the foregoing step (0.857 g, 1.04 mmol) in absolute ethanol (10 ml) cooled to 0° C., and the reaction mixture is stirred overnight. The mixture is then diluted with water, ethanol is evaporated off and the pH is brought to 3 by the addition of citric acid. The acidic mixture is extracted with AcOEt (4×60 ml), the organic extracts are combined, washed with a saturated NaCl aqueous solution and then with water up to neutral pH, the organic phase is dried over $MgSO_4$ and the organic solvent is evaporated off yielding [(2 R,S)-2-carboxy-6-(tert-butoxy-carbonyl-amino)]hexanoyl-L-prolyl-[$N^2$-(2,3,6-tri-methyl-4-methoxy-phenyl)sulphonyl]-L-arginine tert-butyl ester (1.03 g).

(j) {(2 R,S)-2-[N-(1-carbamyl-2-tert-butoxy-propyl)-carbamyl]-6-tert-butoxy-carbonyl-amino]hexanoyl-L-prolyl-($N^G$-(2,3,6-trimethyl-4-methoxy-phenyl)-sulphonyl)-L-arginine tert-butyl ester ($H_2$N-D-Thr($Bu^t$)-(R,S)mLys($N^\epsilon$-Boc)-L-Pro-L-Arg(-$N^G$-Mtr)--O$Bu^t$)

A solution of HOBT (0.194 g, 1.43 mmol) in DMF (1 ml) and $CH_2Cl_2$ (2 ml) is added to a solution of the compound obtained in the foregoing step (1.03 g, 1.3 mmol) in $CH_2Cl_2$ (30 ml) cleared by filtration. The reaction mixture is then cooled to 0° C. and DCCI (0.268 g, 1.3 mmol) is added thereto. The mixture is stirred at 0° C. for 30 minutes and at room temperature for further 20 minutes. The mixture is filtered into a reaction vessel containing a solution of the compound obtained in step (b) (0.333 g, 1.9 mmol) in $CH_2Cl_2$ (30 ml) and stirred overnight. The solvent is evaporated off to dryness, the residue is taken up in THF (10 ml) and the solution is cooled to −17° C. for 2 hours. The DCU which precipitates is removed by filtration and the solution is brought to dryness yielding a clear, light yellow, oil which is dissolved in AcOEt (6 ml) and washed with 5% aqueous $NaHCO_3$ (4×100 ml), 5% aqueous citric acid and then with water up to neutral pH. The organic solution is dried over $MgSO_4$ and the solvent is evaporated off yielding a white foam (1.25 g). This product is purified by flash chromatography using a silica column and eluting with 60% n-hexane/acetone. The thus obtained product is freeze-dried and employed as such in the following step.

(k) {(2R,S)-2-[N-(1-carbamyl-2-hydroxypropyl)carbamyl]-6-amino}hexanoyl-L-prolyl-L-arginine ($H_2$N-D-Thr-(R,S)mLys-L-Pro-L-Arg-OH)

The compound obtained in the foregoing step is dissolved in TFA (20 ml) containing 6% thioanisole and the thus obtained solution is stirred at room temperature for 4 hours. TFA and thioanisole are then allowed to evaporate off by passing a nitrogen stream throughout the mixture, the residue is taken up in $CH_3$CN and concentrated to dryness under vacuum. The residue is taken up again in water containing a few drops of $CH_3$CN. It is washed with $Et_2$O (2×30 ml), $Et_2$O is evaporated off from the aqueous phase which is then freeze-dried.

The thus obtained raw product is purified by column chromatography eluting with $CH_3COONH_4$ $2\times10^{-2}M/CH_3CN$ 0.5%.

(l) {(2R,S)-2-[N-(1-amino-2-hydroxvpropyl)carbamyl]-6-amino}hexanoyl-L-prolyl-L-arginine gThr-(R,S)mLys-L-Pro-L-Arg-OH A solution of the compound obtained in the foregoing step (0.02 mmol) in DMF is added to a solution of TIB (0.024 mmol) in DMF/$H_2$O 4/1 (10 ml) and the obtained reaction mixture is kept at 20° C. under a nitrogen stream for 16 hours.

DMF is then removed and the aqueous phase is freeze-dried. The thus obtained product is purified by reversed-phase chromatography on a Lichroprep RP-18 column (40 g) eluting first with $H_2$O/TFA 1%/$CH_3$CN 3% (540 ml) and then with $H_2$O/TFA 1%/$CH_3$CN 75% (360 ml) and checking the eluted fractions by HPLC. Fractions containing only the desired product are combined. The product isolated therefrom, which as shown by tlc and HPLC analyses is a unitary product, has the following amino acid composition (upon acid hydrolysis at 118° C. for 18 hours):

| Thr | Pro | Arg |
|---|---|---|
| / | 1.01 | 1.00 |

By following substantially the same procedure described in the foregoing example, or the general methods taught in the descriptive portion, and starting from the corresponding compounds of formulas II and III, the following compounds are obtained:

gThr-(R,S)mArg-Pro-Arg-OH
gThr-(S)mArg-Pro-Arg-OH
gThr-(S)mArg-Pro-Arg-OMe
gThr-(S)mLys-Pro-Arg-ONa
gMet-(R,S)mLys-Pro-Arg-OH
gMet-(S)mLys-Pro-Arg-OH
gLeu-(S)mLys-Pro-Arg-OH
For-gLeu-(S)mLys-Pro-Arg-ONa
For-gThr-(S)mLys-Pro-Arg-OH

We claim:
1. A compound of general formula I

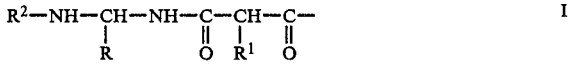

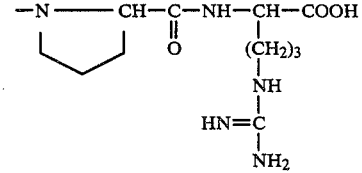

wherein
R represents the side-chain of the amino acids threonine, methionine or leucine,
$R^1$ represents the side-chain of the amino acids lysine or arginine, and
$R^2$ is a hydrogen atom or a metabolically labile acyl group,
and the corresponding pharmacologically acceptable salts, esters and amides.

2. A compound as in claim 1 wherein $R^2$ is hydrogen.
3. A compound as in claim 2 wherein $R^1$ represents the side-chain of the amino acid lysine.
4. A compound as in claim 3 wherein R represents the side-chain of the amino acid threonine.
5. A compound as in claim 4 which is the {2-[N-(1-amino-2-hydroxypropyl)carbamyl]-6-amino}hexanoyl-prolyl-arginine.
6. A pharmaceutical composition comprising an immunostimulating effective amount of the peptides of claims 1, 2, 3, 4 or 5 alone or in combination with a pharmaceutically acceptable carrier.
7. A compound of general formula IV

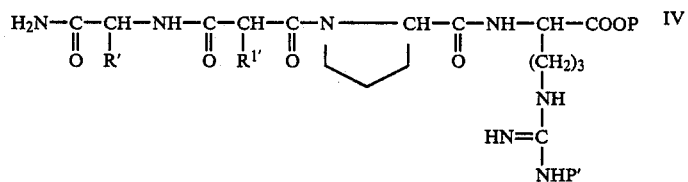
wherein R', R¹', P, and P' are as defined in claim 6 and the corresponding derivatives wherein the protecting groups have been removed.
8. A compound of claim 7 which is {2-[N-(1-carbamyl-2-hydroxy-propyl)carbamyl]-6-amino}hexanoyl-L-prolyl-L-arginine.
* * * * *